US011497563B2

(12) United States Patent
Erkamp et al.

(10) Patent No.: US 11,497,563 B2
(45) Date of Patent: Nov. 15, 2022

(54) SYNCHRONIZED TRACKING OF MULTIPLE INTERVENTIONAL MEDICAL DEVICES

(71) Applicant: KONINKLIJKE PHILIPS N.V., Eindhoven (NL)

(72) Inventors: Ramon Quido Erkamp, Swampscott (NL); Hendrik Roelof Stapert, Eindhoven (NL); Gunther Lamparter, Eindhoven (NL); Ameet Kumar Jain, Boston, MA (US); Alvin Chen, Cambridge, MA (US); Shyam Bharat, Arlington, MA (US); Kunal Vaidya, Boston, MA (US); Francois Guy Gerard Marie Vignon, Andover, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 0 days.

(21) Appl. No.: 17/059,811

(22) PCT Filed: Jun. 6, 2019

(86) PCT No.: PCT/EP2019/064792
§ 371 (c)(1),
(2) Date: Nov. 30, 2020

(87) PCT Pub. No.: WO2019/238526
PCT Pub. Date: Dec. 19, 2019

(65) Prior Publication Data
US 2021/0205025 A1    Jul. 8, 2021

Related U.S. Application Data

(60) Provisional application No. 62/685,301, filed on Jun. 15, 2018.

(51) Int. Cl.
*A61B 34/20* (2016.01)
*A61B 8/08* (2006.01)
*A61B 8/00* (2006.01)

(52) U.S. Cl.
CPC ............ *A61B 34/20* (2016.02); *A61B 8/0841* (2013.01); *A61B 8/463* (2013.01); *A61B 8/467* (2013.01);
(Continued)

(58) Field of Classification Search
CPC ....... A61B 34/20; A61B 8/0841; A61B 8/463; A61B 8/467; A61B 8/54; A61B 2034/2063; A61B 8/4254
See application file for complete search history.

(56) References Cited

U.S. PATENT DOCUMENTS

| 6,122,538 A | 9/2000 | Sliwa, Jr. et al. |
| 8,670,816 B2 | 3/2014 | Green et al. |

(Continued)

FOREIGN PATENT DOCUMENTS

| CN | 106890006 A | 6/2017 |
| WO | 2014018983 A1 | 1/2014 |
| WO | 2014207666 A1 | 12/2014 |
| WO | 2016009350 A1 | 1/2016 |

OTHER PUBLICATIONS

PCT/EP2019/064792 ISR & WO, Jul. 29, 2019, 14 Page Amendment.

*Primary Examiner* — Keith M Raymond
*Assistant Examiner* — Nicholas A Robinson

(57) ABSTRACT

A controller (240/340) for simultaneously tracking multiple interventional medical devices includes a memory (242/342) that stores instructions and a processor (241/341) that executes the instructions. When executed by the processor (241/341), the instructions cause the controller to execute a process that includes receiving timing information from a (Continued)

first signal emitted from an ultrasound probe (252/352) and reflective of timing when the ultrasound probe (252/352) transmits ultrasound beams to generate ultrasound imagery. The process executed by the controller also includes forwarding the timing information to be available for use by a first acquisition electronic component (232/332). The first acquisition electronic component (232/332) also receives sensor information from a first passive ultrasound sensor (S1) on a first interventional medical device (212/312). The timing information is used to synchronize the sensor information from the first passive ultrasound sensor (S1) on the first interventional medical device (212/312) with sensor information from a second passive ultrasound sensor (S2) on a second interventional medical device (216/316).

14 Claims, 7 Drawing Sheets

(52) U.S. Cl.
CPC ........ *A61B 8/54* (2013.01); *A61B 2034/2063* (2016.02)

(56) References Cited

U.S. PATENT DOCUMENTS

| | | | |
|---|---|---|---|
| 9,107,698 B2 | 8/2015 | Razzaque et al. | |
| 2012/0265054 A1 | 10/2012 | Olson | |
| 2013/0237811 A1 | 9/2013 | Mihailescu et al. | |
| 2013/0317347 A1* | 11/2013 | Kwiat | A61B 8/523 600/417 |
| 2014/0222803 A1 | 8/2014 | Bar-Tal et al. | |
| 2015/0173706 A1 | 6/2015 | Andrews et al. | |
| 2016/0203608 A1 | 7/2016 | Izmirli et al. | |
| 2016/0367322 A1* | 12/2016 | Jain | G01S 15/899 |
| 2017/0360395 A1 | 12/2017 | Razzaque et al. | |
| 2020/0397400 A1* | 12/2020 | Chen | A61B 34/20 |

* cited by examiner

SYNCHRONIZED TRACKING OF MULTIPLE INTERVENTIONAL MEDICAL DEVICES

CROSS-REFERENCE TO PRIOR APPLICATIONS

This application is the U.S. National Phase application under 35 U.S.C. § 371 of International Application No. PCT/EP2019/064792, filed on Jun. 6, 2019, which claims the benefit of U.S. Provisional Patent Application No. 62/685,301, filed on Jun. 15, 2018. These applications are hereby incorporated by reference herein.

BACKGROUND

Interventional medical devices such as needles are tracked using ultrasound probes that transmit ultrasound beams to the interventional medical devices. Localization of interventional medical devices in ultrasound images is hampered by the fact that many interventional medical devices lack echogenic properties, and are therefore poorly visible in an ultrasound image. To resolve this issue, a piezo-electric sensor can be applied on an interventional medical device, preferably close to the device tip insofar as a user is typically interested in the location of the device tip. The piezo-electric sensors are passive ultrasound sensors (e.g., PZT, PVDF, copolymer or other piezoelectric material) and are placed on or in the interventional medical devices. The passive ultrasound sensor passively listens to the incident ultrasound waves of the ultrasound beams without responding as the ultrasound beams sweep the field of view of a diagnostic ultrasound B-mode imaging field. Analysis of the resultant signals yields the position of the passive ultrasound sensor on the interventional medical device in the frame of reference of the ultrasound image. The position of the device tip can then be overlaid on the ultrasound image for enhanced visualization of the interventional medical device, and the positions and their histories can be logged for tracking, segmentation, and other applications. An example of such tracking may involve tracking of needle tips of peripheral nerve block needles in 2-dimensional (2D) ultrasound. An interventional medical device is typically tracked using a single ultrasound probe.

FIG. 1 illustrates a known system for tracking an interventional medical device using a passive ultrasound sensor. In FIG. 1, an ultrasound probe 102 emits an imaging beam 103 that sweeps across a passive ultrasound sensor 104 on a tool tip of an interventional medical device 105. Here, interventional medical device 105 may be the needle. An image of tissue 107 is fed back by the ultrasound probe 102. A location of the passive ultrasound sensor 104 on the tool tip of the interventional medical device 105 is provided as a tip location 108 upon determination by a signal processing algorithm. The tip location 108 is overlaid on the image of tissue 107 as an overlay image 109. The image of tissue 107, the tip location 108, and the overlay image 109 are all displayed on a display 100.

SUMMARY

According to an aspect of the present disclosure, a controller for simultaneously tracking multiple interventional medical devices includes a memory that stores instructions and a processor that executes the instructions. When executed by the processor, the instructions cause the controller to execute a process that includes receiving timing information from a first signal emitted from an ultrasound probe and reflective of timing when the ultrasound probe transmits ultrasound beams to generate ultrasound imagery. The process executed by the controller also includes forwarding the timing information to be available for use by a first acquisition electronic component. The first acquisition electronic component also receives sensor information from a first passive ultrasound sensor on a first interventional medical device. The timing information is used to synchronize the sensor information from the first passive ultrasound sensor on the first interventional medical device with sensor information from a second passive ultrasound sensor on a second interventional medical device.

According to another aspect of the present disclosure, a method for simultaneously tracking multiple interventional medical devices includes receiving, at a controller, timing information from a first signal emitted from an ultrasound probe and reflective of timing when the ultrasound probe transmits acoustic beams to generate ultrasound imagery. The method also includes forwarding the timing information to be available for use by a first acquisition electronic component. The first acquisition electronic component also receives sensor information from a first passive ultrasound sensor on a first interventional medical device. The timing information is used to synchronize the sensor information from the first passive ultrasound sensor on the first interventional medical device and sensor information from a second passive ultrasound sensor on a second interventional medical device with ultrasound images from the ultrasound probe.

According to still another aspect of the present disclosure, a system for simultaneously tracking multiple interventional medical devices includes a first interventional medical device, a second interventional medical device, an ultrasound probe, and a controller. The ultrasound probe captures imagery in a space that includes the first interventional medical device and the second interventional medical device. The controller includes a memory that stores instructions and a processor that executes the instructions. When executed by the processor, the instructions cause the controller to execute a process that includes receiving timing information from a first signal emitted from the ultrasound probe and reflective of timing when the ultrasound probe transmits acoustic beams to generate ultrasound imagery. The process executed by the controller also includes forwarding the timing information to be available for use by a first acquisition electronic component. The first acquisition electronic component also receives sensor information from a first passive ultrasound sensor on the first interventional medical device. The timing information is used to synchronize the sensor information from the first passive ultrasound sensor on the first interventional medial device and sensor information from a second passive ultrasound sensor on a second interventional medical device with ultrasound images from the ultrasound probe.

BRIEF DESCRIPTION OF THE DRAWINGS

The example embodiments are best understood from the following detailed description when read with the accompanying drawing figures. It is emphasized that the various features are not necessarily drawn to scale. In fact, the dimensions may be arbitrarily increased or decreased for clarity of discussion. Wherever applicable and practical, like reference numerals refer to like elements.

DETAILED DESCRIPTION

Figure 1:
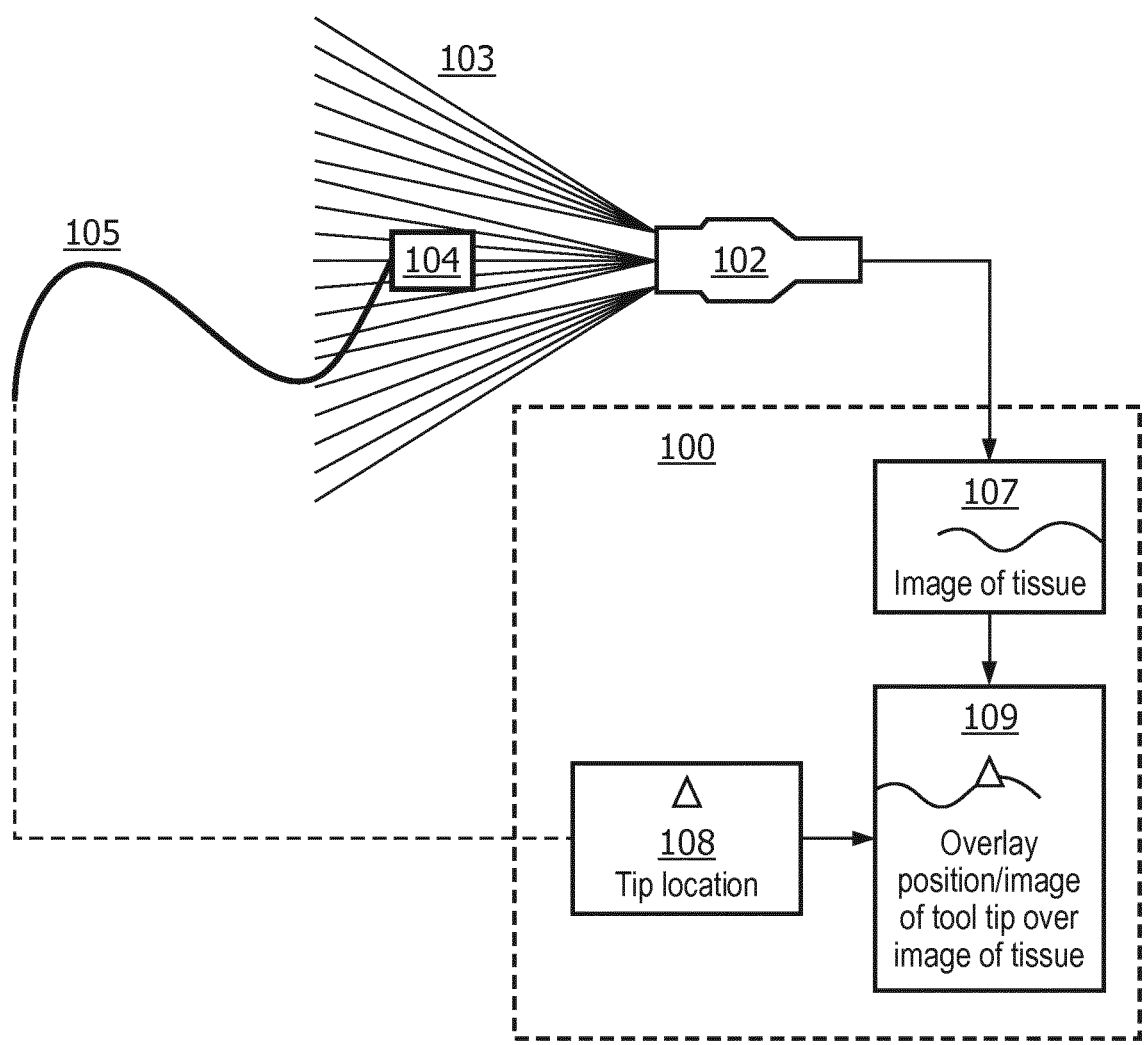
FIG. 1 illustrates a known system for tracking an interventional medical device using a passive ultrasound sensor, in accordance with a representative embodiment.

In the following detailed description, for purposes of explanation and not limitation, representative embodiments disclosing specific details are set forth in order to provide a thorough understanding of an embodiment according to the present teachings. Descriptions of known systems, devices, materials, methods of operation and methods of manufacture may be omitted so as to avoid obscuring the description of the representative embodiments. Nonetheless, systems, devices, materials and methods that are within the purview of one of ordinary skill in the art are within the scope of the present teachings and may be used in accordance with the representative embodiments. It is to be understood that the terminology used herein is for purposes of describing particular embodiments only, and is not intended to be limiting. The defined terms are in addition to the technical and scientific meanings of the defined terms as commonly understood and accepted in the technical field of the present teachings.

It will be understood that, although the terms first, second, third etc. may be used herein to describe various elements or components, these elements or components should not be limited by these terms. These terms are only used to distinguish one element or component from another element or component. Thus, a first element or component discussed below could be termed a second element or component without departing from the teachings of the inventive concept.

The terminology used herein is for purposes of describing particular embodiments only, and is not intended to be limiting. As used in the specification and appended claims, the singular forms of terms 'a', 'an' and 'the' are intended to include both singular and plural forms, unless the context clearly dictates otherwise. Additionally, the terms "comprises", and/or "comprising," and/or similar terms when used in this specification, specify the presence of stated features, elements, and/or components, but do not preclude the presence or addition of one or more other features, elements, components, and/or groups thereof. As used herein, the term "and/or" includes any and all combinations of one or more of the associated listed items.

Unless otherwise noted, when an element or component is said to be "connected to", "coupled to", or "adjacent to" another element or component, it will be understood that the element or component can be directly connected or coupled to the other element or component, or intervening elements or components may be present. That is, these and similar terms encompass cases where one or more intermediate elements or components may be employed to connect two elements or components. However, when an element or component is said to be "directly connected" to another element or component, this encompasses only cases where the two elements or components are connected to each other without any intermediate or intervening elements or components.

In view of the foregoing, the present disclosure, through one or more of its various aspects, embodiments and/or specific features or sub-components, is thus intended to bring out one or more of the advantages as specifically noted below. For purposes of explanation and not limitation, example embodiments disclosing specific details are set forth in order to provide a thorough understanding of an embodiment according to the present teachings. However, other embodiments consistent with the present disclosure that depart from specific details disclosed herein remain within the scope of the appended claims. Moreover, descriptions of well-known apparatuses and methods may be omitted so as to not obscure the description of the example embodiments. Such methods and apparatuses are within the scope of the present disclosure.

Figure 2:
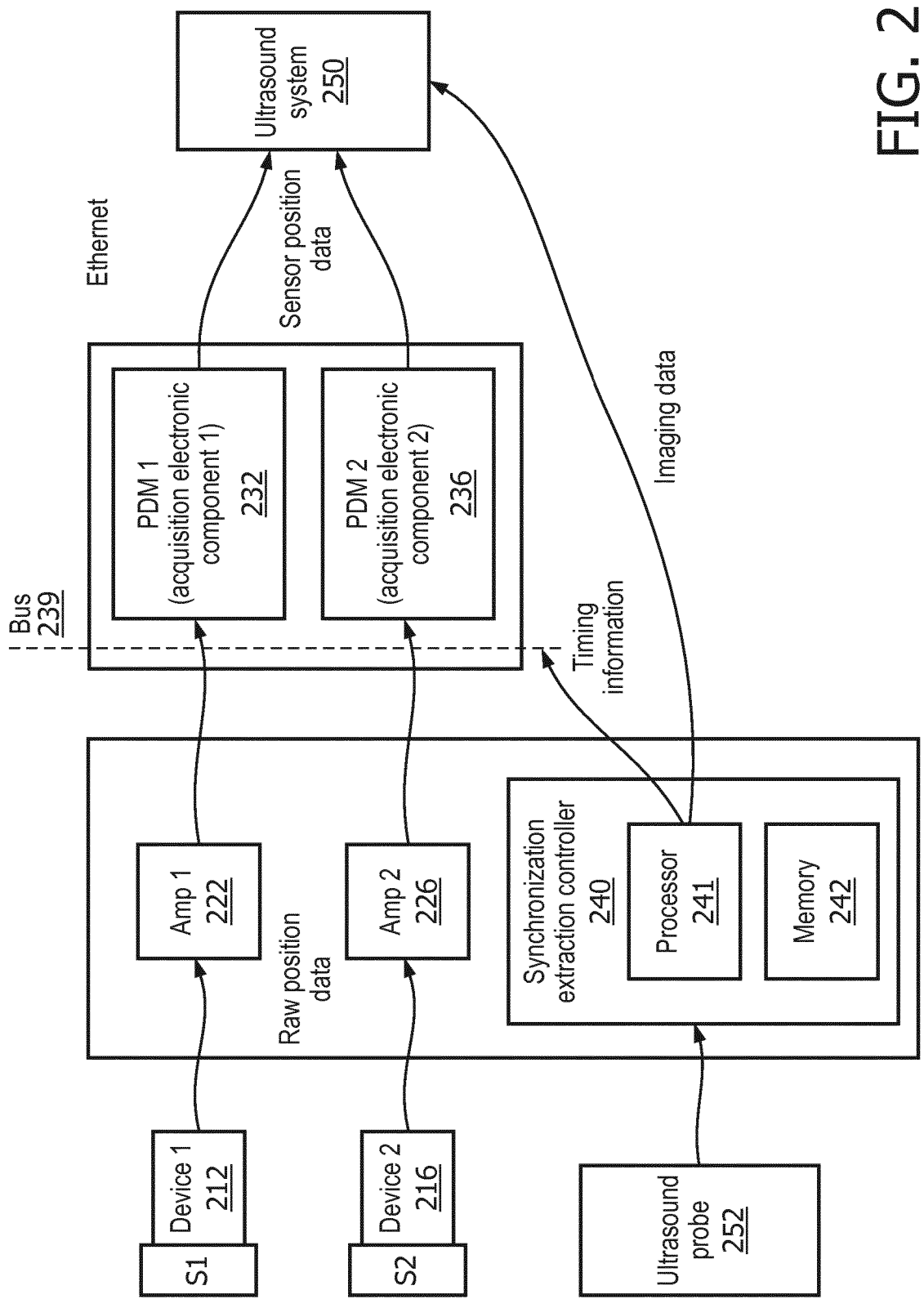
FIG. 2 illustrates a system for synchronized tracking of multiple interventional medical devices, in accordance with a representative embodiment.

FIG. 2 illustrates a system for synchronized tracking of multiple interventional medical devices, in accordance with a representative embodiment.

In FIG. 2, a first interventional medical device 212 (Device1) is provided with a first passive ultrasound sensor S1. A second interventional medical device 216 (Device2) is provided with a second passive ultrasound sensor S2. The first interventional medical device 212 is connected to a first amplifier 222 (Amp1) which amplifies raw sensor data and provides the amplified raw sensor data to first acquisition electronic component 232 (PDM1 (Acquisition electronic component1)). The second interventional medical device 216 is connected to a second amplifier 226 (Amp2) which amplifies raw sensor data and provides the amplified raw sensor data to second acquisition electronic component 236 (PDM2 (Acquisition electronic component2)).

In FIG. 2, two interventional medical devices and supporting elements are shown. However, more than two interventional medical devices, sensors, passive ultrasound sensors, amplifiers and acquisitions electronics may be used in another embodiment, to synchronize tracking of more than two passive ultrasound sensors. Additionally, while each interventional medical device is shown with a single corresponding passive ultrasound sensor, any interventional medical device may be provided with multiple passive ultrasound sensors that are used together, or even a single passive ultrasound sensor with multiple distinct elements. Multiple passive ultrasound sensors or a multi-element passive ultrasound sensor can be used, for example, to identify the shape or orientation of the interventional medical device.

The first acquisition electronic component 232 determines the location of the first passive ultrasound sensor S1 by processing the amplified raw sensor data from the first passive ultrasound sensor S1. The second acquisition electronic component 236 determines the location of the second passive ultrasound sensor S2 by processing the amplified raw sensor data from the second passive ultrasound sensor S2. The location of the first passive ultrasound sensor S1 and the location of the second passive ultrasound sensor S2 are provided to the ultrasound system 250 by ethernet connections in the embodiment of FIG. 2. Each of the first acquisition electronic component 232 and the second acquisition electronic component 236 may be provided with a processor or equivalent that processes instructions to process amplified raw sensor data. A variety of types of processors or similar elements that may be used to implement the first acquisition electronic component 232 and the second acquisition electronic component 236 are described with respect to the processor 510 of FIG. 5 described below.

Separately, the ultrasound probe 252 provides timing information and imaging data to the synchronization extraction controller 240. The timing information may be line triggers and frame triggers from the ultrasound probe 252. Specifically, in the course of creating an ultrasound image the ultrasound probe 252 may sequentially send out individual acoustic beams in different directions, and also create the line triggers and frame triggers as signals to indicate the timing of the transmission of the acoustic beams. The synchronization extraction controller 240 has a memory 242 that stores instructions and a processor 241 that executes the instructions to implement methods as described herein.

In FIG. 2, the synchronization extraction controller 240 may be a controller that implements a process including receiving timing information from a first signal emitted from the ultrasound probe 252 and reflective of timing when the ultrasound probe 252 transmits ultrasound beams to generate ultrasound imagery. Specifically, the timing information may be correlated with an individual ultrasound image generated based on an ultrasound beam transmitted by the ultrasound probe 252. The synchronization extraction controller 240 extracts the timing information (sync info) and provides the timing information to a bus 239. The imaging data is sent from the synchronization extraction controller 240 to the ultrasound system 250.

A notable aspect of the embodiment of FIG. 2 is that the synchronization extraction controller 240 extracts the timing information from the ultrasound probe 252, and provides the timing information to the bus 239. The timing information is correlated with an individual image of the imaging data from the ultrasound probe 252. The first acquisition electronic component 232 uses the timing information to synchronize the location of the first passive ultrasound sensor S1 at the timing of the individual image of the imaging data. The second acquisition electronic component 236 uses the timing information to synchronize the location of the second passive ultrasound sensor S2 at the timing of the individual image of the imaging data. Accordingly, in FIG. 2, at least two electronic components (i.e., the first acquisition electronic component 232 and the second acquisition electronic component 236) separately use the timing information to synchronize sensor information from different passive ultrasound sensors on different interventional medical devices. As a result, the location of the first passive ultrasound sensor S1 and the location of the second passive ultrasound sensor S2 are each synchronized, albeit indirectly, together, and directly to the individual images of the imaging data. As a result, the location of the first interventional medical device 212 and the second interventional medical device 216 can be displayed by the ultrasound system 250 at a proper timing together with the corresponding ultrasound image of the ultrasound imagery.

The first acquisition electronic component 232 in FIG. 2 is representative of a first acquisition electronic component that also receives sensor information from a first passive ultrasound sensor S1 on a first interventional medical device 212. The timing information may be available for use by the first acquisition electronic component 232 can be used to synchronize the sensor information from the first passive ultrasound sensor S1 on the first interventional medical device 212 with sensor information from a second passive ultrasound sensor S2 on the second interventional medical device 216. The timing information can be used to synchronize the sensor information from the first passive ultrasound sensor S1 on the first interventional medical device 212 and the sensor information from the second passive ultrasound sensor S2 on the second interventional medical with individual ultrasound images from the ultrasound probe 252. Additionally, the timing information forwarded from the synchronization extraction controller 240 can be forwarded to the bus 239 to be available for use by both the first acquisition electronic component 232 and a second acquisition electronic component 236.

In FIG. 2, the synchronization extraction controller 240 is implemented in a signal path intermediate the ultrasound probe 252 and a first acquisition electronic component 232 and in a signal path intermediate the ultrasound probe 252 and a second acquisition electronic component 236.

In the embodiment of FIG. 2, the first passive ultrasound sensor S1 and the second passive ultrasound sensor S2 are of the type used to track interventional medical devices. Passive ultrasound sensor data, by design, uniquely links a passive ultrasound sensor to an interventional medical device since the passive ultrasound sensor and the interventional medical device are physically connected or integrated, and physically connected to the electronics on which a signal detection algorithm runs to calculate the location of the passive ultrasound sensor. The sensor data from the first passive ultrasound sensor S1 and the second passive ultrasound sensor S2 is all synced with timing information such as line triggers and frame triggers from the ultrasound probe 252. As a result, the first passive ultrasound sensor S1 and the second passive ultrasound sensor S2 are synchronized together with the ultrasound probe 252. The timing information that controls the synchronization is from the ultrasound probe 252, and may be the line triggers and frame triggers corresponding to each emission of an ultrasound beam from the ultrasound probe 252.

The sensor data from the first passive ultrasound sensor S1 and the second passive ultrasound sensor S2 is provided over a physical connection to the first acquisition electronic component 232 and the second acquisition electronic component 236 respectively. A signal detection algorithm runs on each of the first acquisition electronic component 232 and the second acquisition electronic component 236 to calculate the coordinates of the corresponding sensor. Each of the first acquisition electronic component 232 and the second acquisition electronic component 236 runs the signal detection algorithm so that the corresponding sensor being tracked can be uniquely identified so as to be identifiable in a user interface of the ultrasound system 250 such as a display that displays the ultrasound imagery. For example, a unique code can be embedded in the first acquisition electronic component 232 and the second acquisition electronic component 236 or units that include the first acquisition electronic component 232 and the second acquisition electronic component 236. In this way, in the embodiments of FIG. 2, a process implemented in the system may include forwarding an identifier specific to the first interventional medical device 212 to the first acquisition electronic component 232, and adding an identifier specific to the second interventional medical device 216 to the sensor information from the second passive ultrasound sensor S2. A user can choose to add a text description to the code, which can be shown on the user interface of the ultrasound system 250, to distinguish between the different passive ultrasound sensors. As a result, multiple different interventional medical devices can be tracked with the passive ultrasound sensors using a distributed synchronization signal from the ultrasound probe 252 to the multiple independent tracking hardware components that each track a different passive ultrasound sensor.

To calculate the sensor location in beam space, the sensor tracking computations in the first acquisition electronic component 232 and the second acquisition electronic component 236 only require timing information such as the frame and line trigger synchronization signals from the ultrasound probe 252, and do not need the image data from the ultrasound probe 252. The output of the sensor location computation from the first acquisition electronic component 232 and the second acquisition electronic component 236 may be the beam number and the distance along that beam. As the ultrasound system 250 has the information to do the scan conversion, calculation of sensor location in beam space is sufficient for the first acquisition electronic component 232 and the second acquisition electronic component 236, and routing image data through the first acquisition electronic component 232 and the second acquisition electronic component 236 is not needed.

Additionally, the first amplifier 222 and the second amplifier 226 may be provided in a small module that sits near the patient. The same module may also include the synchronization extraction controller 240 that extracts the trigger signals from the ultrasound imaging data stream without modifying the data stream. Thus, the first amplifier 222, the second amplifier 226 and the synchronization extraction controller 240 may be included in (provided as) a single unit, such as within a single housing or physically connected by dedicated wired connections.

The imaging stream is then directly routed to the ultrasound system 250, while the extracted trigger signals and amplified sensor signals are routed to the first acquisition electronic component 232 and the second acquisition electronic component 236. The first acquisition electronic component 232 and the second acquisition electronic component 236 may be provided separately, or may be provided as a modular tracking module that is modular in nature. For instance, a single tracking module may be provided with ports to track two, three, four or even more different interventional medical devices. Alternatively, for each individual sensor signal, an independent module can be provided with analog to digital conversion, a digital input for the trigger signals, and a digital signal processing unit that includes processor 241 and memory 242 for the sensor tracking locations. The trigger inputs of the independent module(s) all connect to the bus 239 that distributes the trigger signals from the synchronization extraction controller 240 to the independent module(s). After calculating beam space sensor locations, the independent module(s) then transmit these coordinates to the ultrasound system 250. This transmission of coordinates can be performed, for example, over a wired Ethernet connection.

In the embodiment of FIG. 2 described above, a process executed by the synchronization extraction controller 240 includes forwarding timing information to the bus 239 to be available for both acquisition electronic components, i.e., the first acquisition electronic component 232 and the second acquisition electronic component 236. The process executed by a processor 241 in the synchronization extraction controller 240 may include forwarding the timing information to be available for use by both a first acquisition electronic component 232, and a second acquisition electronic component 236. The first acquisition electronic component 232 also receives the sensor information from the first passive ultrasound sensor S1, and the second acquisition electronic component 236 also receives the sensor information from the second passive ultrasound sensor S2 on the second interventional medical device 216.

Figure 3:
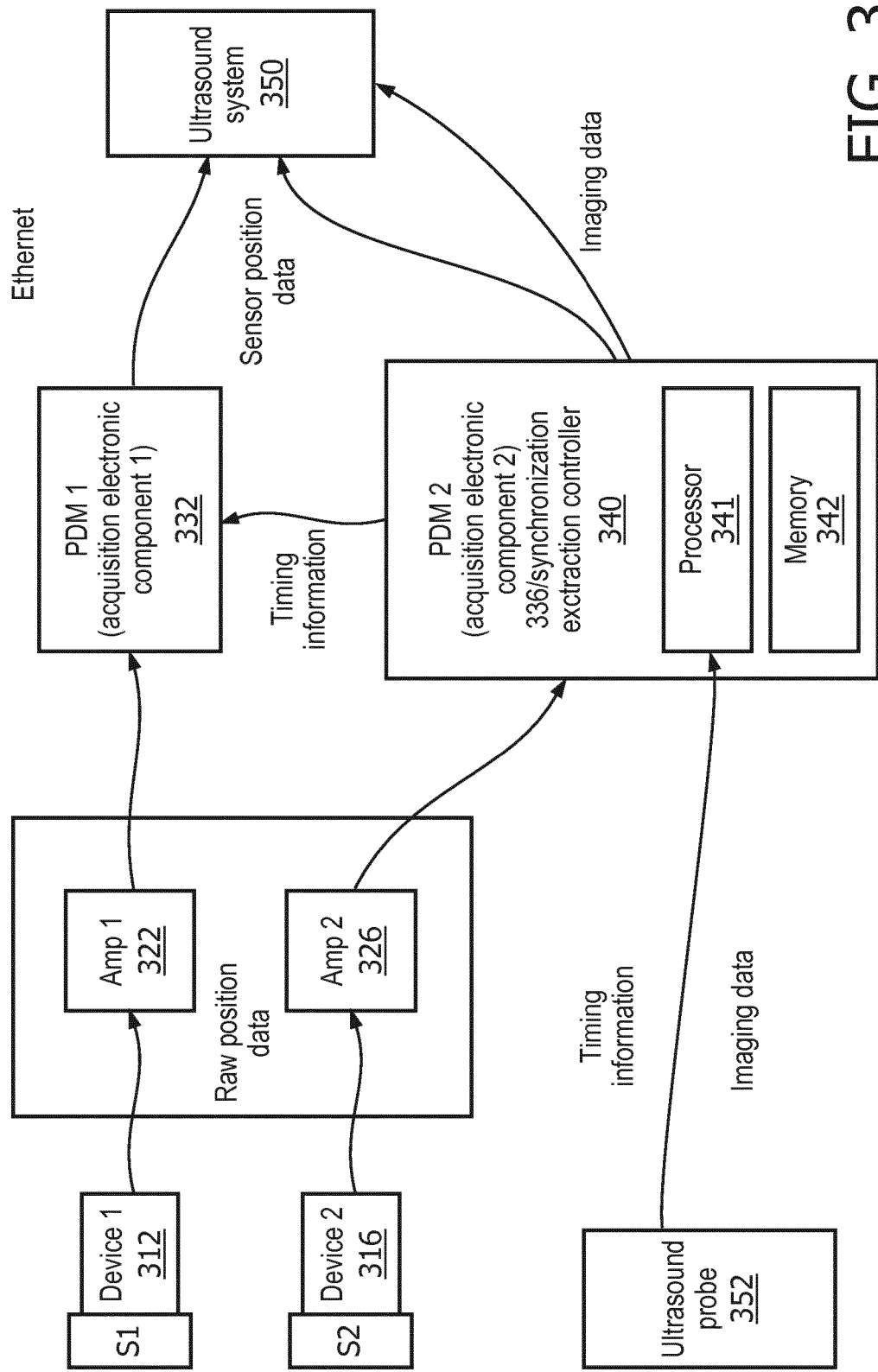
FIG. 3 illustrates another system for synchronized tracking of multiple interventional medical devices, in accordance with a representative embodiment.

FIG. 3 illustrates another system for synchronized tracking of multiple interventional medical devices, in accordance with a representative embodiment.

In FIG. 3, a first interventional medical device 312 (Device1) is provided with a first passive ultrasound sensor S1. A second interventional medical device 316 (Device2) is provided with a second passive ultrasound sensor S2. The first interventional medical device 312 is connected to a first amplifier 322 (Amp1) which amplifies raw sensor data and provides the amplified raw sensor data to first acquisition electronic component 332 (PDM1 (Acquisition electronic component1 in FIG. 3). The second interventional medical device 316 is connected to a second amplifier 326 (Amp2) which amplifies raw sensor data and provides the amplified raw sensor data to second acquisition electronic component 336 (PDM2 (Acquisition electronic component2 in FIG. 3). In the embodiment of FIG. 3, the second acquisition electronic component 336 is integrated into (or with) a synchronization extraction controller 340 that includes a processor 341 and a memory 342. The memory 342 stores instructions, and the processor 341 executes the instructions to implement methods described herein.

The first acquisition electronic component 332 determines the location of the first passive ultrasound sensor S1 by processing the amplified raw sensor data from the first passive ultrasound sensor S1. The second acquisition electronic component 336 determines the location of the second passive ultrasound sensor S2 by processing the amplified raw sensor data from the second passive ultrasound sensor S2. The location of the first passive ultrasound sensor S1 and the location of the second passive ultrasound sensor S2 are provided to the ultrasound system 350 by ethernet connections in the embodiment of FIG. 3. Each of the first acquisition electronic component 332 and the second acquisition electronic component 336 may be provided with a processor or equivalent that processes instructions to process amplified raw sensor data. A variety of types of processors or similar elements that may be used to implement the first acquisition electronic component 332 and the second acquisition electronic component 336 are described with respect to the processor 510 of FIG. 5 described below.

Separately, the ultrasound probe 352 provides timing information and imaging data to the synchronization extraction controller 340 that incorporates the second acquisition electronic component 336. As noted, the synchronization extraction controller 340 has a memory 342 that stores instructions and a processor 341 that executes the instructions to implement methods described herein. The synchronization extraction controller 340 extracts the timing information (sync info) for use by the second acquisition electronic component 336, and also forwards or otherwise provides the timing information to the first acquisition electronic component 332 for us by the first acquisition electronic component 332. The imaging data is sent from the synchronization extraction controller 340 to the ultrasound system 350.

A notable aspect of the embodiment of FIG. 3 is that the timing information is daisy chained to the synchronization extraction controller 340 (for use by the second acquisition electronic component 3336) and then to the first acquisition electronic component 332. In comparison to the embodiment of FIG. 2, there is no bus 239, and the synchronization extraction controller 340 is not provided as an element entirely separate from either of the second acquisition electronic component 336 and the first acquisition electronic component 332, since the second acquisition electronic component 336 is incorporated in the synchronization extraction controller 340. Moreover, in the embodiment of FIG. 3, the ultrasound probe 352 is only connected to one of the acquisition electronic component, i.e., the second acquisition electronic component, but the data path with the timing information is passed through to all acquisition electronic components.

As in the embodiment of FIG. 2, in the embodiment of FIG. 3 the timing information is correlated with an individual image of the imaging data from the ultrasound probe 352. The first acquisition electronic component 332 uses the timing information to synchronize the location of the first passive ultrasound sensor S1 at the timing of the individual image of the imaging data. The second acquisition electronic component 336 uses the timing information to synchronize the location of the second passive ultrasound sensor S2 at the timing of the individual image of the imaging data. As a result, the location of the first passive ultrasound sensor S1 and the location of the second passive ultrasound sensor S2 are each synchronized, albeit indirectly, together, and directly to the individual images of the imaging data. As a result, the location of the first interventional medical device 312 and the second interventional medical device 316 can be displayed by the ultrasound system 350 at a proper timing.

The first acquisition electronic component 332 in FIG. 3 is representative of a first acquisition electronic component that also receives sensor information from a first passive ultrasound sensor S1 on a first interventional medical device 312. The timing information may be available for use by the first acquisition electronic component 332 and can be used to synchronize the sensor information from the first passive ultrasound sensor S1 on the first interventional medical device 312 with sensor information from a second passive ultrasound sensor S2 on the second interventional medical device 316. The timing information can be used to synchronize the sensor information from the first passive ultrasound sensor S1 on the first interventional medical device 312 and the sensor information from the second passive ultrasound sensor S2 on the second interventional medical device 316 with individual ultrasound images from the ultrasound probe 352. Additionally, the timing information received by a second acquisition electronic component 336 is forwarded from the synchronization extraction controller 340 for use by the first acquisition electronic component 332.

In the embodiment of FIG. 3, a first passive ultrasound sensor S1 and a second passive ultrasound sensor S2 are of the type used for sensor tracking systems to track the first interventional medical device 312 and the second interventional medical device 316 respectively. The sensor data from the first passive ultrasound sensor S1 and the second passive ultrasound sensor S2 on the different interventional medical devices is all synced with timing information such as line and frame triggers from the ultrasound probe 352. As a result, the first passive ultrasound sensor S1 and the second passive ultrasound sensor S2 are synchronized together, along with the ultrasound probe 252. The controlling timing information is from the ultrasound probe 352, and may be the line and frame triggers corresponding to each emission from the ultrasound probe 352.

In FIG. 3, the second acquisition electronic component 336 receives the timing information before the first acquisition electronic component 332. Insofar as a timing difference thus exists, a process may be introduced for correcting for the timing difference between the second acquisition electronic component 336 and the first acquisition electronic component 332 by adding a delay to the timing information at the synchronization extraction controller 340 for use in synchronizing the sensor information. Additionally, insofar as the timing information in FIG. 3 is used to synchronise sensor information from different passive ultrasound sensors, the second acquisition electronic component 336 and the first acquisition electronic component 332 each forward sensor information from the second passive ultrasound sensor S2 and the first passive ultrasound sensor S1, respectively, to the ultrasound system (350).

As noted above for the embodiment of FIG. 2, signal detection algorithms are run by acquisition electronic components so that the corresponding sensor being tracked can be uniquely identified so as to be identifiable in a user interface. Similarly, in the embodiment of FIG. 3, a unique code or identifier can be embedded in the first acquisition electronic component 332 and the second acquisition electronic component 336 or units that include the first acquisition electronic component 332 and the second acquisition electronic component 336. In this way, in the embodiment of FIG. 3, a process implemented in the system may include forwarding an identifier specific to the first interventional medical device 312 to the first acquisition electronic component 332, and adding an identifier specific to the second interventional medical device 316 to the sensor information from the second passive ultrasound sensor S2. As a result, multiple different interventional medical devices can be tracked with the passive ultrasound sensors using a distributed synchronization signal from the ultrasound probe 352 to the multiple independent sensor tracking hardware components that each track a different passive ultrasound sensor.

In the embodiment of FIG. 3, the synchronization extraction controller 340 only has to forward the timing information to a single acquisition electronic component, i.e., the first acquisition electronic component 332, since the synchronization extraction controller 340 is already integrated with the second acquisition electronic component 336. In contrast, in the embodiment of FIG. 2, the synchronization extraction controller 240 forwards the timing information to the bus 239 to be available for both acquisition electronic components, i.e., the first acquisition electronic component 232 and the second acquisition electronic component 236. Thus, in the embodiment of FIG. 2, a process executed by the synchronization extraction controller 240 includes forwarding the timing information to be available for use by a second acquisition electronic component 236, wherein the second acquisition electronic component 236 also receives the sensor information from the second passive ultrasound sensor S2 on the second interventional medical device 216.

Figure 4:
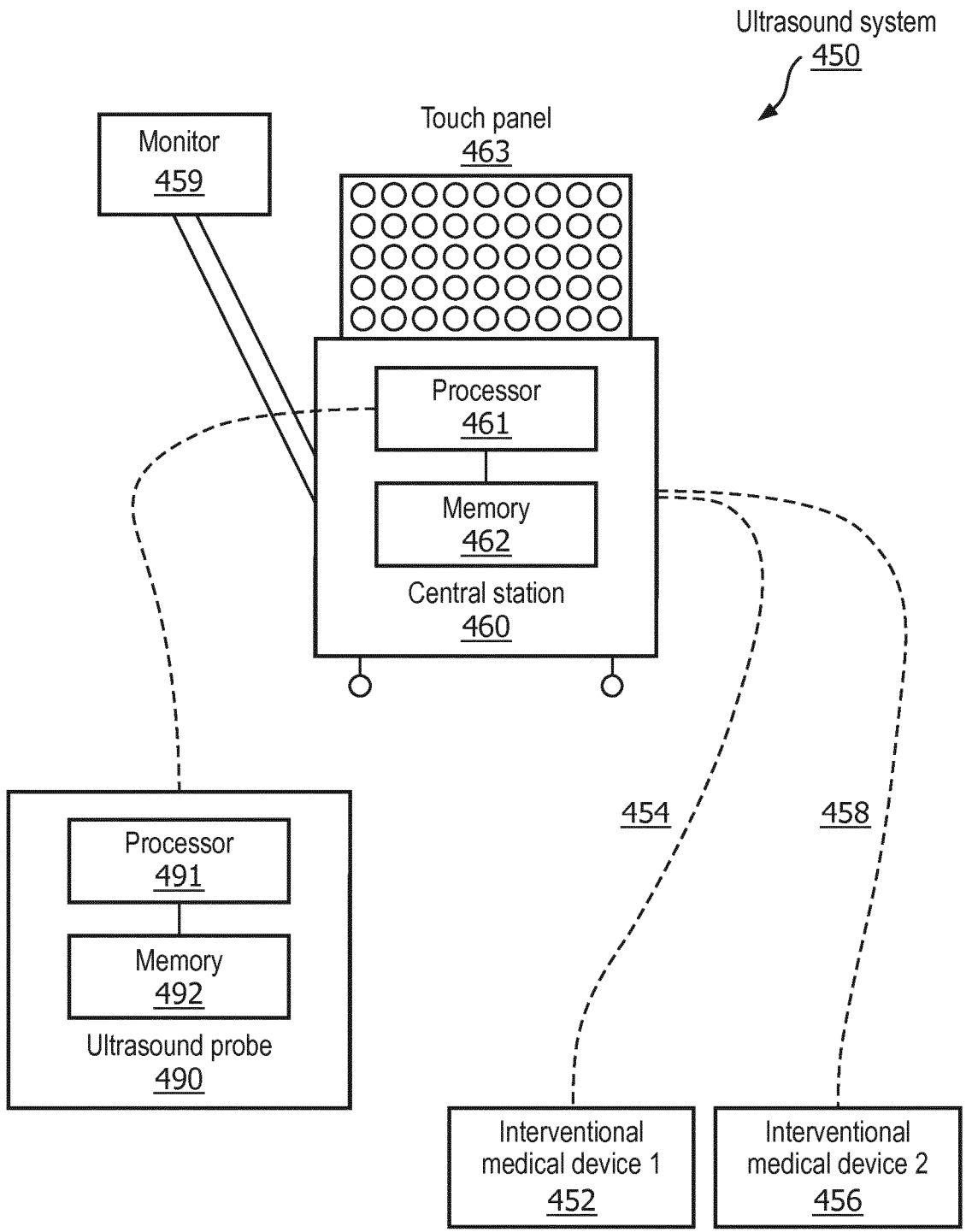
FIG. 4 illustrates another system for synchronized tracking of multiple interventional medical devices, in accordance with a representative embodiment.

FIG. 4 illustrates another system for synchronized tracking of multiple interventional medical devices, in accordance with a representative embodiment.

In FIG. 4, an ultrasound system 450 includes a central station 460 with a processor 461 and memory 462, a touch panel 463, a monitor 459, an second interventional medical device 456 connected to the central station 460 by a data connection 458 (e.g., a wired or wireless data connection), and a first interventional medical device 452 connected to the central station 460 by a data connection 454 (e.g., a wired or wireless data connection). The central station 460 includes a memory 462 that stores instructions and a processor 461 that executes the instructions. An ultrasound probe 490 includes a memory 492 that stores instructions and a processor 491 that executes the instructions.

A "controller" as described herein, may be implemented by at least the processor 461 and memory 462 in the central station 460, or by the processor 491 and memory 492 in the ultrasound probe 490. A "controller" may also be implemented by a processor/memory combination separate from the central station 460 and ultrasound probe 490, such as by a module used to implement the second acquisition electronic component 336 integrated with the synchronization extraction controller in FIG. 3, or by a module used to implement the synchronization extraction controller 240 in FIG. 2. That is, a "controller" as described herein may be implemented in a variety of forms, either by modifying an existing system or type of system, or by providing a new system or type of system such as a stand-alone module used to extract and coordinate timing information from an ultrasound probe.

The first interventional medical device 452 may be provided at the end of a wire or similar instrument. The second interventional medical device 456 may also or alternatively be provided at the end of a wire or similar instrument. The first interventional medical device 452 may be, for example, an intravascular ultrasound probe that produces ultrasound imagery, though sensor signals from a first passive ultrasound sensor S1 on the first interventional medical device 452 are the signals of interest relative to the first interventional medical device 452 for the purposes of this description. The second interventional medical device 456 may also or alternatively be, for example, an intravascular ultrasound probe that produces ultrasound imagery, though sensor signals from a second passive ultrasound sensor S2 on the second interventional medical device 456 are the signals of interest relative to the second interventional medical device 456 for the purposes of this description.

More particularly, in the embodiment of FIG. 4, a passive ultrasound sensor S1 and a passive ultrasound sensor S2 may be separately provided on the first interventional medical device 452 and the second interventional medical device 456, respectively. The passive ultrasound sensor signals from the passive ultrasound sensor S1 and the passive ultrasound sensor S2 are synchronized with ultrasound imagery from the ultrasound probe 490. Time-of-flight measurements provide the axial/radial distance of the passive ultrasound sensor S1 and the passive ultrasound sensor S2 from the ultrasound probe 490. Amplitude measurements and knowledge of the beam firing sequence may provide the lateral position of the passive ultrasound sensor S1 and the passive ultrasound sensor S2. Since phase can correspond to time-of-flight, phase may be used instead of time-of-flight insofar as phase may provide higher measurement precision.

When multiple PZT elements are provided for the passive ultrasound sensor S1 and/or the passive ultrasound sensor S2, the measurements can be averaged to provide an overall position of the first interventional medical device 452 and/or the second interventional medical device 456. Additionally, since relative positional arrangements of the PZT elements may be known in this case, the overall relative pose, 3-dimensional directionality, and even a predicted trajectory of the first interventional medical device 452 and/or the second interventional medical device 456 can also be determined from the relative measurements.

By way of explanation, the first interventional medical device 452 and the second interventional medical device 456 are each placed internally into a patient during a medical procedure. Locations of the first interventional medical device 452 and the second interventional medical device 456 can be seen on imagery generated by the ultrasound probe 490.

In the embodiment of FIG. 4, a synchronization controller can be implemented in the central station 460, to extract timing information from the ultrasound probe 490 and synchronize individual images from the ultrasound probe 490 with locations of the first interventional medical device 452 and the second interventional medical device 456. In this case, the central station 460 may functionally and/or physically replace the first acquisition electronic component 332 and the second acquisition electronic component 336 integrated with the synchronization extraction controller 340 in the embodiment of FIG. 3. The central station 460 may also functionally and/or physically replace the first acquisition electronic component 232 and the second acquisition electronic component 236 in the embodiment of FIG. 5.

Figure 5:
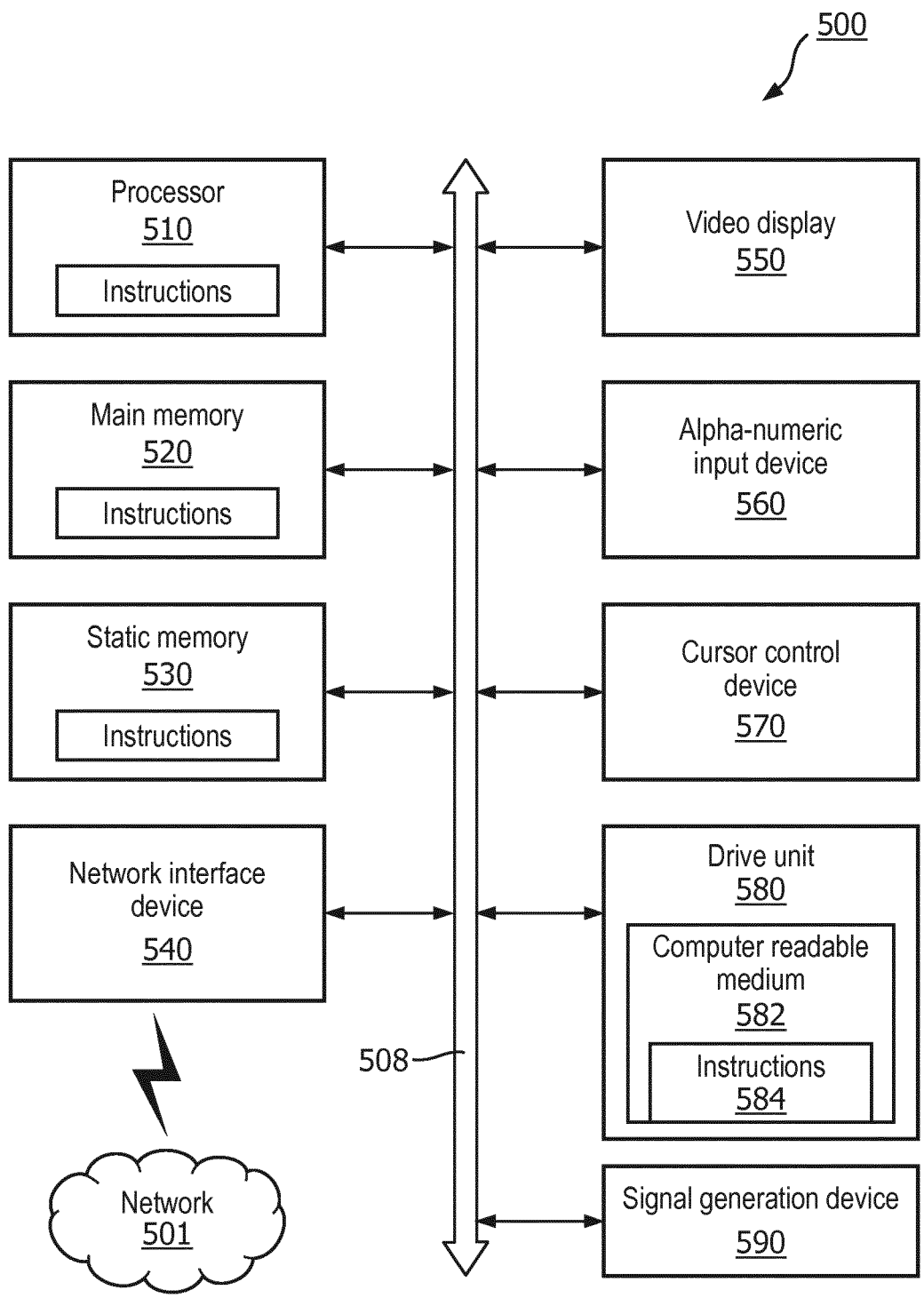
FIG. 5 is an illustrative embodiment of a general computer system, on which a method of synchronized tracking of multiple interventional medical devices can be implemented, in accordance with a representative embodiment.

FIG. 5 is an illustrative embodiment of a general computer system, on which a method of synchronized tracking of multiple interventional medical devices can be implemented, in accordance with a representative embodiment.

The computer system 500 can include a set of instructions that can be executed to cause the computer system 500 to perform any one or more of the methods or computer based functions disclosed herein. The computer system 500 may operate as a standalone device or may be connected, for example, using a network 501, to other computer systems or peripheral devices. Any or all of the elements and characteristics of the computer system 500 in FIG. 5 may be representative of elements and characteristics of the central station 460, the first interventional medical device 452, the second interventional medical device 456, the second interventional medical device 456, the first interventional medical device 452, or other similar devices and systems that can include a controller and perform the processes described herein.

In a networked deployment, the computer system 500 may operate in the capacity of a client in a server-client user network environment. The computer system 500 can also be fully or partially implemented as or incorporated into various devices, such as an ultrasound probe, a controller, a synchronization extraction controller, an ultrasound system, acquisition electronic component, a central station, a control station, a passive ultrasound sensor, a stationary computer, a personal computer (PC), or any other machine capable of executing a set of instructions (sequential or otherwise) that specify actions to be taken by that machine. The computer system 500 can be incorporated as or in a device that in turn is in an integrated system that includes additional devices. In an embodiment, the computer system 500 can be implemented using electronic devices that provide video or data communication. Further, while the computer system 500 is illustrated, the term "system" shall also be taken to include any collection of systems or sub-systems that individually or jointly execute a set, or multiple sets, of instructions to perform one or more computer functions.

As illustrated in FIG. 5, the computer system 500 includes a processor 510. A processor 510 for a computer system 500 is tangible and non-transitory. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. Any processor described herein is an article of manufacture and/or a machine component. A processor for a computer system 500 is configured to execute software instructions to perform functions as described in the various embodiments herein. A processor for a computer system 500 may be a general-purpose processor or may be part of an application specific integrated circuit (ASIC). A processor for a computer system 500 may also be a microprocessor, a microcomputer, a processor chip, a controller, a microcontroller, a digital signal processor (DSP), a state machine, or a programmable logic device. A processor for a computer system 500 may also be a logical circuit, including a programmable gate array (PGA) such as a field programmable gate array (FPGA), or another type of circuit that includes discrete gate and/or transistor logic. A processor for a computer system 500 may be a central processing unit (CPU), a graphics processing unit (GPU), or both. Additionally, any processor described herein may include multiple processors, parallel processors, or both. Multiple processors may be included in, or coupled to, a single device or multiple devices.

Moreover, the computer system 500 includes a main memory 520 and a static memory 530 that can communicate with each other via a bus 508. Memories described herein are tangible storage mediums that can store data and executable instructions, and are non-transitory during the time instructions are stored therein. As used herein, the term "non-transitory" is to be interpreted not as an eternal characteristic of a state, but as a characteristic of a state that will last for a period. The term "non-transitory" specifically disavows fleeting characteristics such as characteristics of a carrier wave or signal or other forms that exist only transitorily in any place at any time. A memory described herein is an article of manufacture and/or machine component. Memories described herein are computer-readable mediums from which data and executable instructions can be read by a computer. Memories as described herein may be random access memory (RAM), read only memory (ROM), flash memory, electrically programmable read only memory (EPROM), electrically erasable programmable read-only memory (EEPROM), registers, a hard disk, a removable disk, tape, compact disk read only memory (CD-ROM), digital versatile disk (DVD), floppy disk, blu-ray disk, or any other form of storage medium known in the art. Memories may be volatile or non-volatile, secure and/or encrypted, unsecure and/or unencrypted.

As shown, the computer system 500 may further include a video display unit 550, such as a liquid crystal display (LCD), an organic light emitting diode (OLED), a flat panel display, a solid-state display, or a cathode ray tube (CRT). Additionally, the computer system 500 may include an input device 560, such as a keyboard/virtual keyboard or touch-sensitive input screen or speech input with speech recognition, and a cursor control device 570, such as a mouse or touch-sensitive input screen or pad. The computer system 500 can also include a disk drive unit 580, a signal generation device 590, such as a speaker or remote control, and a network interface device 540.

In an embodiment, as depicted in FIG. 5, the disk drive unit 580 may include a computer-readable medium 582 in which one or more sets of instructions 584, e.g. software, can be embedded. Sets of instructions 584 can be read from the computer-readable medium 582. Further, the instructions 584, when executed by a processor, can be used to perform one or more of the methods and processes as described herein. In an embodiment, the instructions 584 may reside completely, or at least partially, within the main memory 520, the static memory 830, and/or within the processor 510 during execution by the computer system 800.

In an alternative embodiment, dedicated hardware implementations, such as application-specific integrated circuits (ASICs), programmable logic arrays and other hardware components, can be constructed to implement one or more of the methods described herein. One or more embodiments described herein may implement functions using two or more specific interconnected hardware modules or devices with related control and data signals that can be communicated between and through the modules. Accordingly, the present disclosure encompasses software, firmware, and hardware implementations. Nothing in the present application should be interpreted as being implemented or implementable solely with software and not hardware such as a tangible non-transitory processor and/or memory.

In accordance with various embodiments of the present disclosure, the methods described herein may be implemented using a hardware computer system that executes software programs. Further, in an exemplary, non-limited embodiment, implementations can include distributed processing, component/object distributed processing, and parallel processing. Virtual computer system processing can be constructed to implement one or more of the methods or functionality as described herein, and a processor described herein may be used to support a virtual processing environment.

The present disclosure contemplates a computer-readable medium 582 that includes instructions 584 or receives and executes instructions 584 responsive to a propagated signal; so that a device connected to a network 501 can communicate video or data over the network 501. Further, the instructions 584 may be transmitted or received over the network 501 via the network interface device 540.

Figure 6:
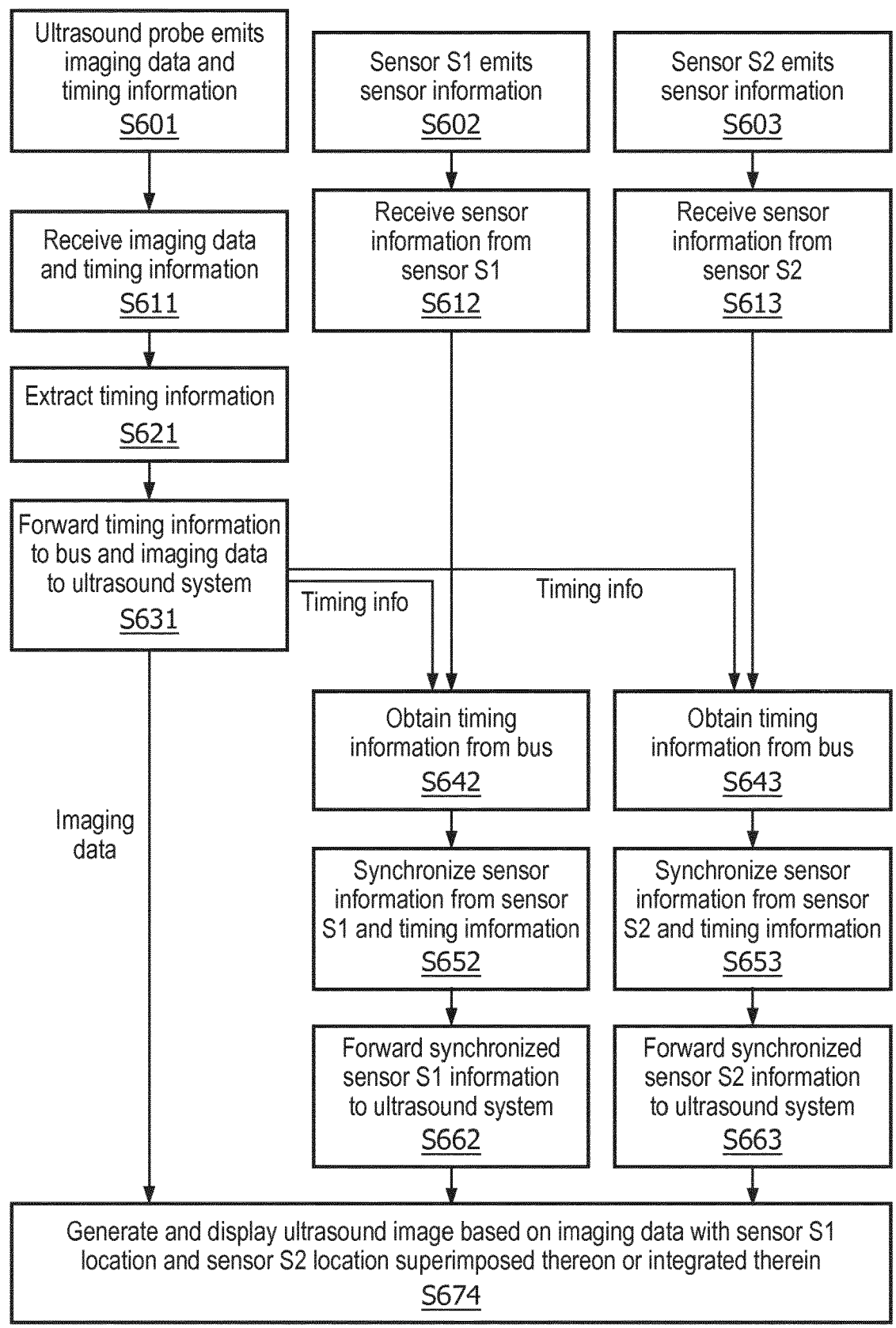
FIG. 6 illustrates a method for synchronized tracking of multiple interventional medical devices using the system of FIG. 2, in accordance with a representative embodiment.

FIG. 6 illustrates a method for synchronized tracking of multiple interventional medical devices, in accordance with a representative embodiment.

In FIG. 6, features of the method are generally organized horizontally and vertically in an organized arrangement which reflects potentially simultaneous or overlapping performance by different elements of a system. For example, at S601 an ultrasound probe emits imaging data and timing information. The emission at S601 is based on reflections of ultrasound imaging beams previously emitted by the ultrasound probe 252. The timing information is reflective of times when beams are emitted from the ultrasound probe, resulting in images corresponding to the imaging data. At the same time or close to the same time as the emission at S601, a passive ultrasound sensor S1 emits sensor information at S602, and the passive ultrasound sensor S2 emits sensor information at S603. The sensor information emitted by sensor S1 at S602 is based on receipt by the passive ultrasound sensor S1 of the beams emitted by the ultrasound probe, and the sensor information emitted by sensor S2 at S603 is also based on receipt by the passive ultrasound sensor S2 of the beams emitted by the ultrasound probe. In other words, the emission at S601 is based on received reflections at the ultrasound probe 252, whereas the emission at S602 and S603 is based on direct receipt of the beams by the first passive ultrasound sensor S1 and the second passive ultrasound sensor S2.

At S611, imaging data and timing information are received from the ultrasound probe. In the embodiment of FIG. 2, the imaging data and timing information are received by the synchronization extraction controller 240, whereas in the embodiment of FIG. 3, the imaging data and timing information are received by the synchronization extraction controller 340 that is implemented with the second acquisition electronic component 336. At S621, the timing information is extracted by whichever element receives the imaging data and timing information in S611.

At S631, the imaging data is forwarded to an ultrasound system 250, whereas the timing information is forwarded to the bus 239 for retrieval by the first acquisition electronic component 232 and the second acquisition electronic component 236. At S642, the first acquisition electronic component 232 obtains the timing information from the bus 239. At S643, the second acquisition electronic component 236 obtains the timing information from the bus 239.

At S652, the first acquisition electronic component 232 synchronizes the sensor information from the first passive ultrasound sensor S1 and the timing information from the ultrasound probe. That is, the sensor information from the first passive ultrasound sensor S1 is correlated with, matched with, set with, labelled with, or otherwise associated with the timing information for a particular image from the ultrasound probe. At S653, the second acquisition electronic component 236 synchronizes the sensor information from the second passive ultrasound sensor S2 and the timing information from the ultrasound probe. That is, the sensor information from the second passive ultrasound sensor S2 is correlated with, matched with, set with, labelled with, or otherwise associated with the timing information for a same particular image from the ultrasound probe. The same image from the ultrasound probe is synchronized with sensor information from each of the first passive ultrasound sensor S1 and the second passive ultrasound sensor S2 at S652 and S653.

At S662, the synchronized sensor information from the first passive ultrasound sensor S1 is forwarded to the ultrasound system 250 by the first acquisition electronic component 232. At S663, the synchronized sensor information from the second passive ultrasound sensor S2 is forwarded to the ultrasound system 250 by the second acquisition electronic component 236.

At S674, the ultrasound system 250 generates and displays the ultrasound image using the imaging data along with the location of the first passive ultrasound sensor S1 and the location of the second passive ultrasound sensor S2 superimposed thereon or integrated therein. When the locations are superimposed, this may be taken to mean, for example, that the ultrasound image is first generated, and then the locations of the first passive ultrasound sensor S1 and the second passive ultrasound sensor S2 replace particular portions of the ultrasound image, such as by using a distinctive color not otherwise used in the ultrasound image. When the locations are integrated with the ultrasound image, this may be taken to mean, for example, that particular portions of the ultrasound image are shaded to be substantially darker or lighter. Moreover, the locations of the first passive ultrasound sensor S1 and the second passive ultrasound sensor S2 may be correlated with the entirety or portions of individual interventional medical devices, so the sensor locations may be displayed as a shape of an interventional medical device such as a needle tip or an end of an intravascular ultrasound probe.

Figure 7:
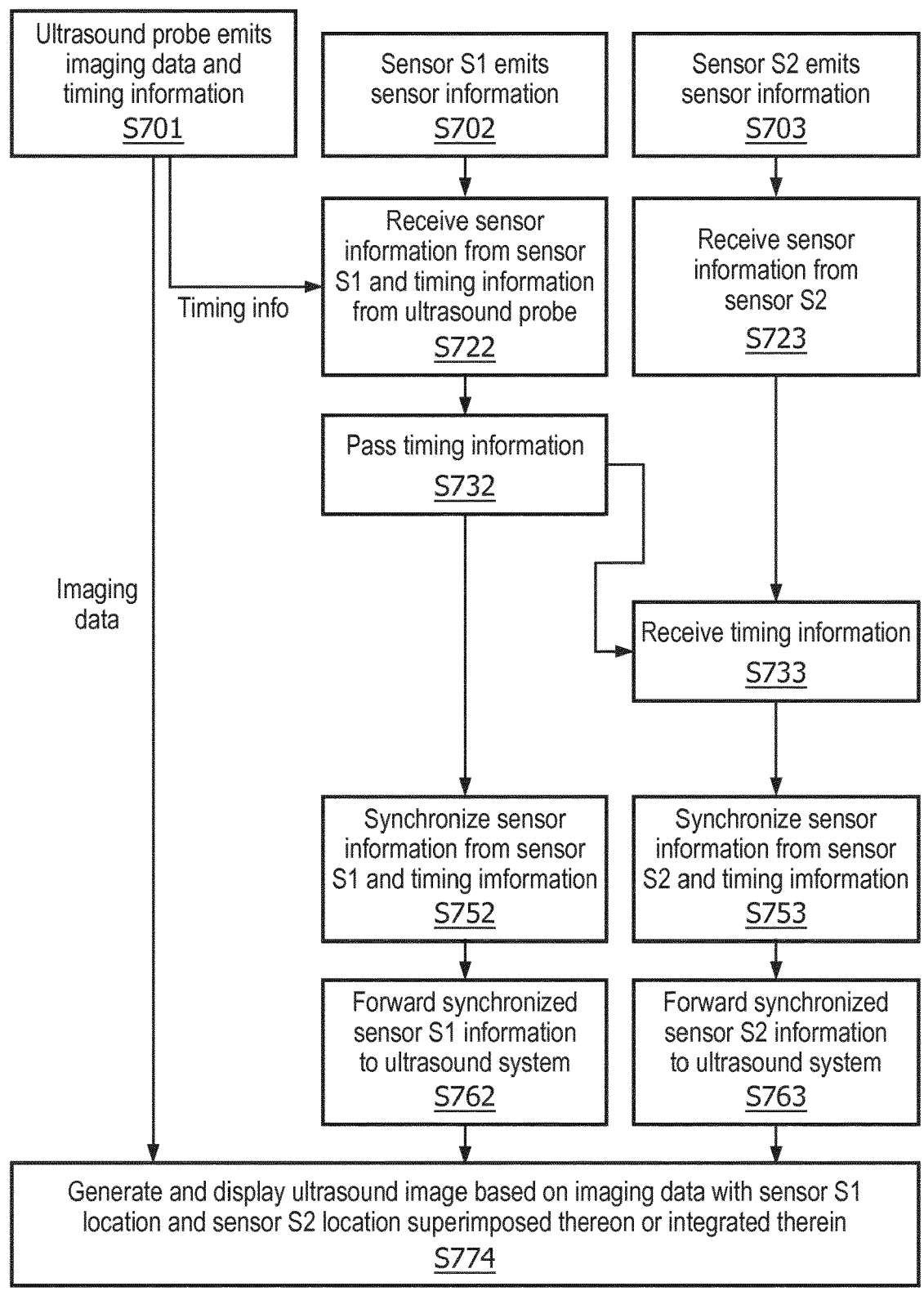
FIG. 7 illustrates another method for synchronized tracking of multiple interventional medical devices using the system of FIG. 3, in accordance with a representative embodiment.

FIG. 7 illustrates another method for synchronized tracking of multiple interventional medical devices, in accordance with a representative embodiment.

In FIG. 7, similar to the embodiment of FIG. 6, features of the method are generally organized horizontally and vertically in an organized arrangement which reflects potentially simultaneous or overlapping performance by different elements of a system. For example, at S701 an ultrasound probe 352 emits imaging data and timing information. The emission at S701 is based on reflections of ultrasound imaging beams previously emitted by the ultrasound probe 352. The timing information is reflective of times when beams are emitted from the ultrasound probe 352, resulting in images corresponding to the imaging data. At the same time or close to the same time as the emission at S701, a passive ultrasound sensor S1 emits sensor information at S702, and the passive ultrasound sensor S2 emits sensor information at S703. The sensor information emitted by sensor S1 at S702 is based on receipt by the passive ultrasound sensor S1 of the beams emitted by the ultrasound probe, and the sensor information emitted by sensor S2 at S703 is also based on receipt by the passive ultrasound sensor S2 of the beams emitted by the ultrasound probe. In other words, the emission at S701 is based on received reflections at the ultrasound probe 352, whereas the emission at S702 and S703 is based on direct receipt of the beams by the first passive ultrasound sensor S1 and the second passive ultrasound sensor S2.

At S722, timing information is received from the ultrasound probe S722 and sensor information is received from the first passive ultrasound sensor S1. The received of sensor information and timing information at S722 is by the second acquisition electronic component 336 that implements the synchronization extraction controller 340 in FIG. 3. At S732, the timing information is passed from the second acquisition electronic component 336 to the first acquisition electronic component 332, and at S733 the first acquisition electronic component 332 receives the timing information. Before the first acquisition electronic component 332 receives the timing information from the second acquisition electronic component 336 at S733, the first acquisition electronic component receives the sensor information from the second passive ultrasound sensor S2 at 5723.

At S752, the first acquisition electronic component 332 synchronizes the sensor information from the first passive ultrasound sensor S1 and the timing information from the ultrasound probe. That is, the sensor information from the first passive ultrasound sensor S1 is correlated with, matched with, set with, labelled with, or otherwise associated with the timing information for a particular image from the ultrasound probe. At S753, the second acquisition electronic component 336 synchronizes the sensor information from the second passive ultrasound sensor S2 and the timing information from the ultrasound probe. That is, the sensor information from the second passive ultrasound sensor S2 is correlated with, matched with, set with, labelled with, or otherwise associated with the timing information for a same particular image from the ultrasound probe. The same image from the ultrasound probe is synchronized with sensor information from each of the first passive ultrasound sensor S1 and the second passive ultrasound sensor S2 at S752 and S753.

At S762, the synchronized sensor information from the first passive ultrasound sensor S1 is forwarded to the ultrasound system 350 by the first acquisition electronic component 332. At S763, the synchronized sensor information from the second passive ultrasound sensor S2 is forwarded to the ultrasound system 350 by the second acquisition electronic component 336.

At S774, the ultrasound system 350 generates and displays the ultrasound image using the imaging data along with the location of the first passive ultrasound sensor S1 and the location of the second passive ultrasound sensor S2 superimposed thereon or integrated therein. When the locations are superimposed, this may be taken to mean, for example, that the ultrasound image is first generated, and then the locations of the first passive ultrasound sensor S1 and the second passive ultrasound sensor S2 replace particular portions of the ultrasound image, such as by using a distinctive color not otherwise used in the ultrasound image. When the locations are integrated with the ultrasound image, this may be taken to mean, for example, that particular portions of the ultrasound image are shaded to be substantially darker or lighter. Moreover, the locations of the first passive ultrasound sensor S1 and the second passive ultrasound sensor S2 may be correlated with the entirety or portions of individual interventional medical devices, so the sensor locations may be displayed as a shape of an interventional medical device such as a needle tip or an end of an intravascular ultrasound probe.

Accordingly, synchronized tracking of multiple interventional medical devices enables multiple devices to be tracked independently in the same ultrasound field, so that they can be resultantly displayed in a 2D or 3D ultrasound image. The accurate device positioning and navigation in real time ultrasound imaging can be used in a variety of procedures. For example, in ablation procedures to treat atrial fibrillation, simultaneous tracking (i.e. in the field of view of the single ultrasound image) of an ablation catheter and the lasso catheter using an intracardiac echocardiography (ICE) catheter (or a transesophageal echocardiography (TEE) probe) may be beneficial. Similarly, in continuous peripheral nerve block (PNB) procedures in which both the PNB needle tip and the catheter tip need to be tracked by extravascular ultrasound, simultaneous tracking (i.e., in the field of view of the single ultrasound image) may be beneficial. Another example use may be in tissue ablation procedures; in that ablation devices can have 3 independent needle tips that all require visibility in ultrasound imaging. As yet another use of the synchronized tracking described herein, an interventional cardiologist may be provided with an ability to put an implantable device (e.g. in a transcatheter aortic valve replacement (TAVR) procedure) on the right location. Both the delivery device (e.g. a guidewire/catheter combination) and the implantable device can be tracked to assess the right location. Finally, active implantable devices (such as implantable cardioverter defibrillators (ICDs) or implantable pressure sensors) may require careful guidance in order to be placed at the right location, and they often need to be removed from the body or replaced. Being able to locate the implantable and guide a device to remove the implantable to the right location may provide a major improvement over current practice.

Although synchronized tracking of multiple interventional medical devices has been described with reference to several exemplary embodiments, it is understood that the words that have been used are words of description and illustration, rather than words of limitation. Changes may be made within the purview of the appended claims, as presently stated and as amended, without departing from the scope and spirit of synchronized tracking of multiple interventional medical devices in its aspects. Although synchronized tracking of multiple interventional medical devices has been described with reference to particular means, materials and embodiments, synchronized tracking of multiple interventional medical devices is not intended to be limited to the particulars disclosed; rather synchronized tracking of multiple interventional medical devices extends to all functionally equivalent structures, methods, and uses such as are within the scope of the appended claims.

The illustrations of the embodiments described herein are intended to provide a general understanding of the structure of the various embodiments. The illustrations are not intended to serve as a complete description of all of the elements and features of the disclosure described herein. Many other embodiments may be apparent to those of skill in the art upon reviewing the disclosure. Other embodiments may be utilized and derived from the disclosure, such that structural and logical substitutions and changes may be made without departing from the scope of the disclosure. Additionally, the illustrations are merely representational and may not be drawn to scale. Certain proportions within the illustrations may be exaggerated, while other proportions may be minimized. Accordingly, the disclosure and the figures are to be regarded as illustrative rather than restrictive.

One or more embodiments of the disclosure may be referred to herein, individually and/or collectively, by the term "invention" merely for convenience and without intending to voluntarily limit the scope of this application to any particular invention or inventive concept. Moreover, although specific embodiments have been illustrated and described herein, it should be appreciated that any subsequent arrangement designed to achieve the same or similar purpose may be substituted for the specific embodiments shown. This disclosure is intended to cover any and all subsequent adaptations or variations of various embodiments. Combinations of the above embodiments, and other embodiments not specifically described herein, will be apparent to those of skill in the art upon reviewing the description.

For example, instead of wired connections, in appropriate circumstances sensor position data can be transmitted wirelessly to an ultrasound system 350 or an ultrasound system 250. Similarly, signals from an ultrasound probe 352 may be transmitted wirelessly throughout a data path or in a limited portion of a data path to an ultrasound system 350 or an ultrasound system 250.

The Abstract of the Disclosure is provided to comply with 37 C.F.R. § 1.72(b) and is submitted with the understanding that it will not be used to interpret or limit the scope or meaning of the claims. In addition, in the foregoing Detailed Description, various features may be grouped together or described in a single embodiment for the purpose of streamlining the disclosure. This disclosure is not to be interpreted as reflecting an intention that the claimed embodiments require more features than are expressly recited in each claim. Rather, as the following claims reflect, inventive subject matter may be directed to less than all of the features of any of the disclosed embodiments. Thus, the following claims are incorporated into the Detailed Description, with each claim standing on its own as defining separately claimed subject matter.

The preceding description of the disclosed embodiments is provided to enable any person skilled in the art to practice the concepts described in the present disclosure. As such, the above disclosed subject matter is to be considered illustrative, and not restrictive, and the appended claims are intended to cover all such modifications, enhancements, and other embodiments which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description.

The invention claimed is:

1. A system for simultaneously tracking multiple interventional medical devices, the system comprising:
 a first interventional medical device configured with a first passive ultrasound sensor;
 a second interventional medical device configured with a second passive ultrasound sensor;
 an ultrasound probe configured to generate ultrasound imagery in a space that includes the first interventional medical device and the second interventional medical device;

a controller configured to:
receive one or more signals emitted from the ultrasound probe and reflective of timing when the ultrasound probe transmits acoustic beams to generate the ultrasound imagery, and
extract timing information from the one or more signals emitted from the ultrasound probe, the timing information comprising trigger signals corresponding to emission of the acoustic beams from the ultrasound probe;
a first acquisition electronic component configured to (i) receive first sensor position data from the first passive ultrasound sensor, (ii) receive the timing information from the controller, and (iii) synchronize a location of the first passive ultrasound sensor to the ultrasound imagery based on the first sensor position data and the timing information; and
a second acquisition electronic component configured to (i) receive second sensor position data from the second passive ultrasound sensor, (ii) receive timing information from the controller, and (iii) synchronize a location of the second passive ultrasound sensor to the ultrasound imagery based on the second sensor position data and the timing information; and
a display configured to display the ultrasound imagery with the synchronized location of the first passive ultrasound sensor and the synchronized location of the second passive ultrasound sensor.

2. The system of claim 1,
wherein the controller is implemented in a signal path intermediate the ultrasound probe and the first acquisition electronic component and intermediate the ultrasound probe and the second acquisition electronic component.

3. The system of claim 1,
wherein the first acquisition electronic component and the second acquisition electronic component separately use the timing information to synchronize sensor position information from different passive ultrasound sensors on different interventional medical devices.

4. The system of claim 3, wherein the controller is further configured to:
forward the ultrasound imagery from the ultrasound probe to an ultrasound system that provides the ultrasound imagery with the synchronized location of the first passive ultrasound sensor and the synchronized location of the second passive ultrasound sensor superimposed thereon.

5. The system of claim 1, wherein the first acquisition electronic component and the second acquisition electronic component each receive sensor position information from different passive ultrasound sensors on different interventional medical devices.

6. The system of claim 1, wherein the timing information corresponds to timing of an individual ultrasound image of the ultrasound imagery generated by the ultrasound probe.

7. The system of claim 1, wherein the controller is implemented in a signal path intermediate the ultrasound probe and the first acquisition electronic component, and the controller is implemented by the second acquisition electronic component.

8. The system of claim 1, wherein the second acquisition electronic component and the first acquisition electronic component each forward sensor position information from different passive ultrasound sensors on different interventional medical devices to an ultrasound system that provides the ultrasound imagery with positions of the first interventional medical device and the second interventional medical device superimposed thereon.

9. The system of claim 1, wherein at least one of the first interventional medical device and the second interventional medical device comprises a needle.

10. The system of claim 1, wherein the controller is further configured to:
forward an identifier specific to the first interventional medical device to the first acquisition electronic component.

11. The system of claim 1, wherein the controller is further configured to:
forward an identifier specific to the first interventional medical device to the first acquisition electronic component; and
add an identifier specific to the second interventional medical device to the second sensor position data from the second passive ultrasound sensor on the second interventional medical device.

12. The system of claim 1, wherein the controller is further configured to:
correct for a timing difference between the second acquisition electronic component and the first acquisition electronic component by adding a delay to the timing information at the controller.

13. The system of claim 1, wherein:
the first acquisition electronic component is configured to determine the location of the first passive ultrasound sensor in a beam space of the ultrasound probe based on the timing information, wherein the determined location of the first passive ultrasound sensor includes a beam number of a corresponding beam emitted from the ultrasound probe and a first distance along the beam, and
the second acquisition electronic component is configured to determine the location of the second passive ultrasound sensor in the beam space of the ultrasound probe based on the timing information, wherein the determined location of the second passive ultrasound sensor includes the beam number of a corresponding beam emitted from the ultrasound probe and a second distance along the beam.

14. The system of claim 1, wherein the trigger signals include at least one of line trigger signals and frame trigger signals corresponding to emission of the acoustic beams from the ultrasound probe.

* * * * *